United States Patent [19]

Middendorf et al.

[11] Patent Number: 5,534,125
[45] Date of Patent: Jul. 9, 1996

[54] DNA SEQUENCING

[75] Inventors: Lyle R. Middendorf; Robert C. Bruce, both of Lincoln; Robert D. Eckles, Malcolm, all of Nebr.

[73] Assignee: Li-Cor, Inc., Lincoln, Nebr.

[21] Appl. No.: 288,461

[22] Filed: Aug. 10, 1994

Related U.S. Application Data

[60] Division of Ser. No. 18,806, Feb. 17, 1993, Pat. No. 5,360,523, which is a continuation-in-part of Ser. No. 763,230, Sep. 20, 1991, Pat. No. 5,230,781, and Ser. No. 570,503, Aug. 21, 1990, Pat. No. 5,207,880, each is a continuation-in-part of Ser. No.78,279, Jul. 27, 1987, abandoned, which is a division of Ser. No. 594,676, Mar. 29, 1984, Pat. No. 4,729,947.

[51] Int. Cl.$^6$ .......................... G01K 27/26; G01N 27/447
[52] U.S. Cl. .......................... 204/618; 204/612; 204/616; 204/608
[58] Field of Search .................... 204/299 R, 182.8; 356/344

[56] References Cited

U.S. PATENT DOCUMENTS

| | | | |
|---|---|---|---|
| 4,116,565 | 9/1978 | Powell et al. | 356/344 |
| 4,675,095 | 6/1987 | Kambara et al. | 356/344 X |
| 4,707,235 | 11/1987 | Englert et al. | 204/299 R X |
| 4,832,815 | 5/1989 | Kambara et al. | 204/299 R |
| 4,874,492 | 10/1989 | Mackay | 204/299 R |
| 4,881,812 | 11/1989 | Ohkube et al. | 204/299 R X |
| 4,957,613 | 9/1990 | Schuette | 204/182.8 X |
| 4,971,677 | 11/1990 | Kambara et al. | 356/344 X |
| 5,043,051 | 8/1991 | Berry et al. | 204/182.8 X |
| 5,051,162 | 9/1991 | Kambara et al. | 204/299 R |
| 5,062,942 | 11/1991 | Kambara et al. | 204/299 R |
| 5,069,769 | 12/1991 | Fujimiya et al. | 204/182.8 |
| 5,100,529 | 3/1992 | Fujii | 356/344 X |
| 5,360,523 | 11/1994 | Middendorf et al. | 204/182.8 |

*Primary Examiner*—John Niebling
*Assistant Examiner*—John S. Starsiak, Jr.
*Attorney, Agent, or Firm*—Vincent L. Carney

[57] ABSTRACT

To sequence DNA, DNA samples marked with flourscent infrared dye are applied at a plurality of locations for electrophoresing in a plurality of channels through a gel electrophoresis slab. The channels are scanned with a laser and a sensor, that include a microscope focused on the gel slab. The focal point and slab are adjusted with respect to each other so that the focal point of the microscope remains on the gel slab during a scan. The data from the scan is directly used to amplitude modulate density readings on a display, and the scan is displayed in a horizontal sweep of a cathode ray tube, whereby said cathode ray tube provides intensity displays of bands representing DNA. Different sizes of glass gel sandwiches may be mounted to the same console for different sequencing tasks.

4 Claims, 12 Drawing Sheets

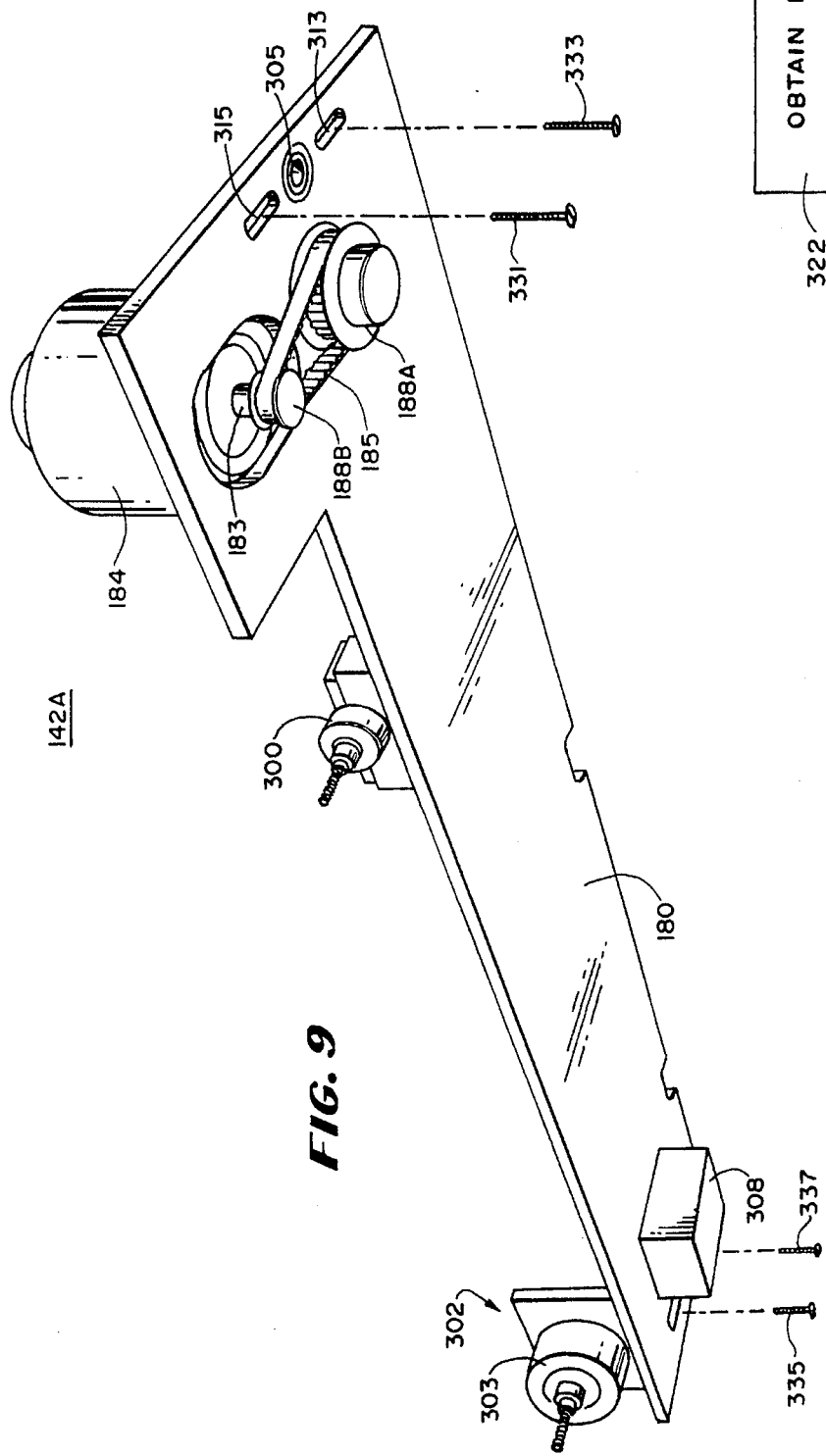
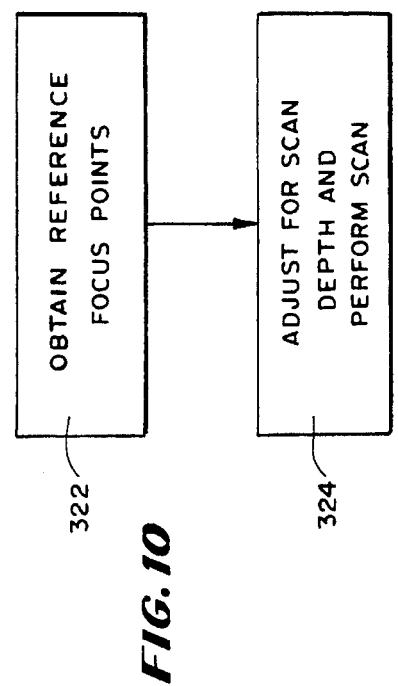
FIG. 9
FIG. 10

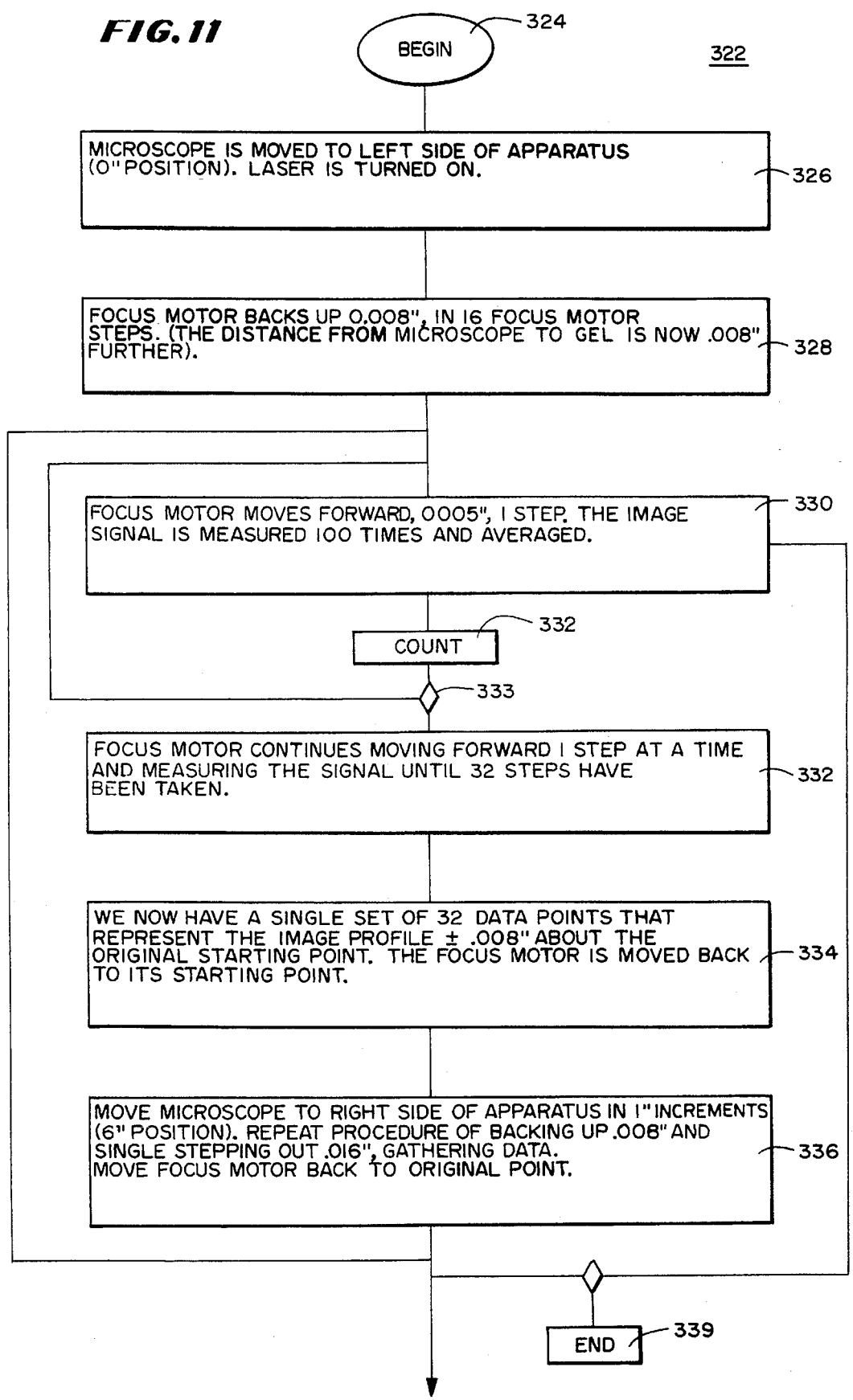

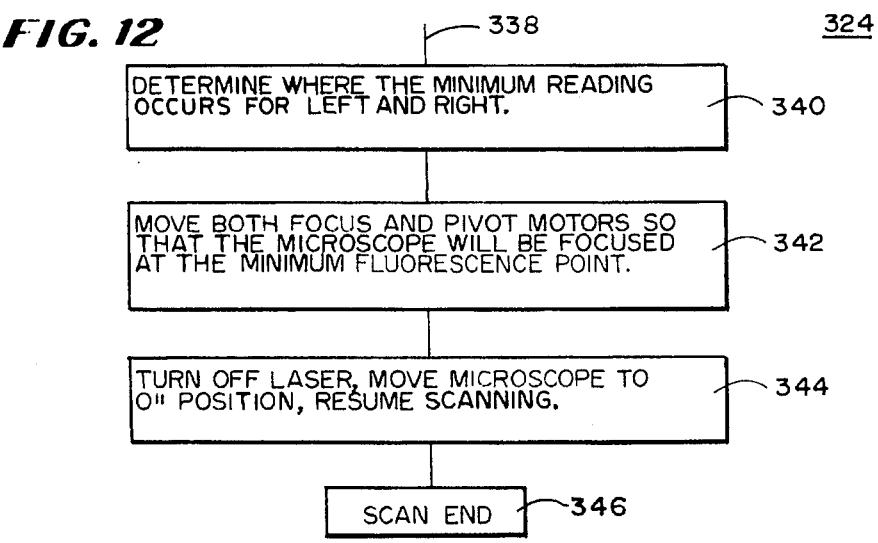
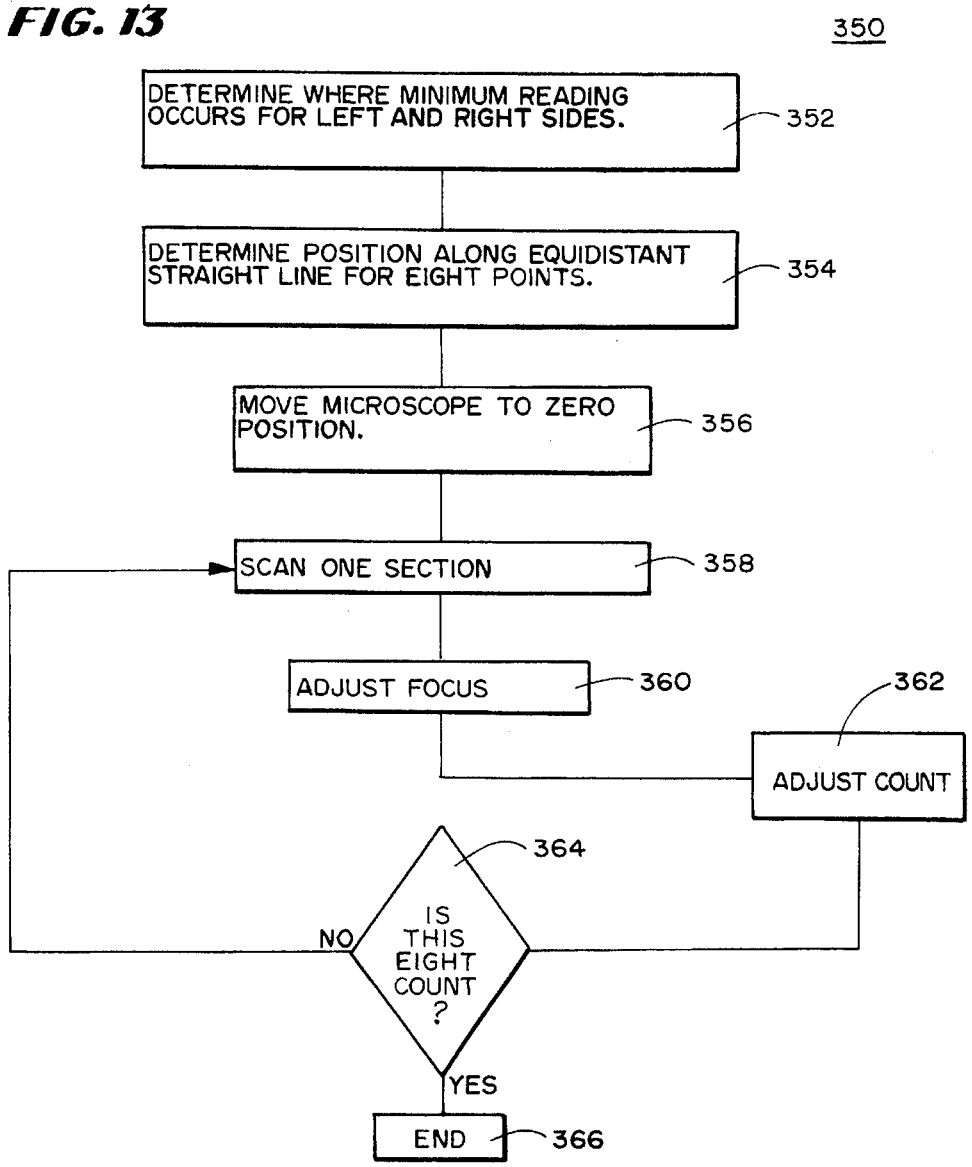

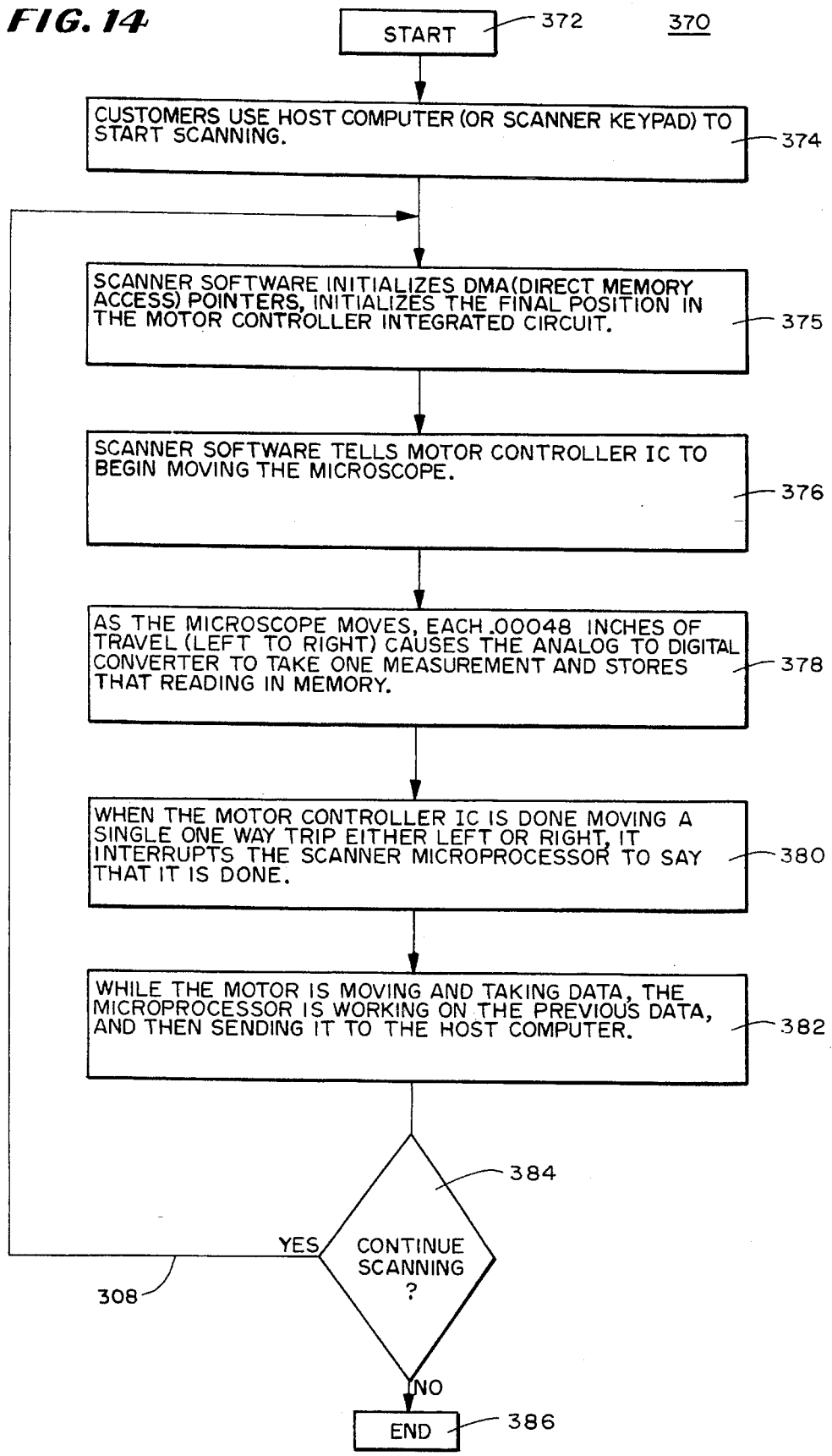

DNA SEQUENCING

REFERENCE TO RELATED APPLICATIONS

This application is a division, of application Ser. No. 08/018,806, filed Feb. 17, 1993, now U.S. Pat. No. 5,360,523 which is a continuation-in-part application of application Ser. No. 07/763,230 filed Sep. 20, 1991, now U.S. Pat. No. 5,230,781 and of application Ser. No. 07/570,503 filed Aug. 21, 1990, now U.S. Pat. No. 5,207,880 which are continuations in part of Ser. No. 07/078,279 filed Jul. 27, 1987, now abandoned which is a division of U.S. application Ser. No. 594,676 for DNA SEQUENCING filed by Middendorf et al. on Mar. 29, 1984, and assigned to the same assignee as this application, now U.S. Pat. No. 4,729,947.

BACKGROUND OF THE INVENTION

This invention relates to the sequencing of DNA strands.

In one class of techniques for sequencing DNA, identical strands of DNA are marked. The strands are separated into four aliquots. The strands in a given aliquot are either individually cleaved at or synthesized to any base belonging to only one of the four base types, which are adenine, guanine, cytosine and thymine (hereinafter A, G, C and T). The adenine-, guanine-, cytosine- and thymine-terminated strands are then electrophoresed for separation. The rate of electrophoresis indicates the DNA sequence.

In a prior art sequencing technique of this class, the DNA strands are marked with a radioactive marker, and after being separated by electrophoresis, film is exposed to the gel and developed to indicate the sequence of the bands. The range of lengths and resolution of this type of static detection is limited by the size of the apparatus.

It is also known in the prior art to use fluorescent markers for marking proteins and to pulse the fluorescent markers with light to receive an indication of the presence of a particular protein from the fluorescence.

The prior art techniques for DNA sequencing have several disadvantages such as: (1) they are relatively slow; (2) they are at least partly manual; and (3) they are limited to relatively short strands of DNA.

SUMMARY OF THE INVENTION

Accordingly, it is an object of the invention to provide a novel technique for DNA sequencing.

It is a still further object of the invention to provide novel apparatuses and methods for sequencing relatively large fragments of DNA.

It is a still further object of the invention to provide novel apparatuses and methods for sequencing DNA fragments of 100 bases or more.

It is a still further object of the invention to provide a technique for continuous sequencing of DNA.

It is a still further object of the invention to continuously sequence DNA without the spatial limitations of range of lengths and resolution.

It is a still further object of the invention to provide a novel technique for continuously sequencing DNA using fluorescent detection.

It is a still further object of the invention to provide a novel technique for DNA sequencing using a fluorescent marker fastened to the DNA, or the inherent fluorescence of the DNA itself.

It is a still further object of the invention to provide a novel technique for continuously sequencing DNA marked with fluorescence which more clearly distinguishes marked DNA fragments from background fluorescence.

It is a still further object of the invention to provide a novel technique for scanning fluorescent material.

It is a still further object of the invention to provide a novel technique for displaying fluorescent material.

In accordance With the above and further objects of the invention, strands of DNA are continuously electrophoresed and identified. For this purpose, the strands are fluorescently marked by direct labelling of fluorescent markers to the strands or by fluorescently labelled probes hybridized to the separated strands. The light emitted while irradiating the strands near the terminal end of the electrophoresis channel is detected and correlated. The electrophoresis conditions are selected so that strands being electrophoresed near the terminal end of the electrophoresis channel are fully resolved prior to the resolution of longer strands which are at the entrance end of the electrophoresis channel, and so on, in a continuous process over a period of time.

The apparatus for such continuously sequencing of DNA includes one or more electrophoresis channels, each adapted to receive fluorescently labeled DNA strands, having at one end a base of a given type. Each of the channels has a path and electrical field across it identical in its characteristics to the path of the other channels and electrical fields across the other channels.

To provide marking, either a fluorescent marker is attached to the DNA fragments prior to their being electrophoresed, or probes are used to combine or hybridize with the DNA strands. In the latter case, the detection is accomplished by detecting a fluorescent marker that is chemically attached to the probe. In the preferred embodiment, the marker is a dye that fluoresces in the infrared or near infrared region.

The electrophoresis may be provided in conventional gel slabs or in tube gels such as gel filled capillary tubes or buffer filled capillary tubes. For the configuration using conventional gel slabs, one embodiment provides for a different input section for each of four channels that are for a corresponding one of the A, G, T and C strands. Other embodiments allow for less than four gel channels by judiciously combining one or more base types A, G, T, or C in a channel. The strands are detected during electrophoresis either in the gel by scanning back and forth across the gel at a fixed distance from the entrance end of the gel or by one or more fixed detectors located at a fixed distance from the entrance end of the gel or after leaving the gel. The strands are detected in a manner that indicates their mobility in the gel to indicate the sequence of the A, G, C and T strands of different lengths.

The detection apparatus includes a light source, such as a laser or arc lamp or other suitable source that emits light in the optimum absorption spectrum of the marker. The light may be split by the use of fiber. In the preferred embodiment, the light source is a diode laser that irradiates the channels with near infrared or infrared light having a wavelength that matches the absorbance region of the marker. The detector includes a light sensor which is preferably an avalanche photodiode sensitive to the near infrared or infrared light emission of the marker. It may include a filtering system having a pass band suitable for passing selectively the optimum emission of the fluorescent marker to the light sensor. Correlation of the channel in which the fluorescent light is detected and the time of detection of the fluorescent light indicates: (1) if the type of base termination or nucleotide cleavage is A, G, C or T or a combination thereof for those embodiments which have more than one base type in a channel; and (2) the time sequence of separation of each strand in each channel of the electrophoresis gel. This information, in turn, indicates the overall sequence of strands.

To use the apparatus to sequence DNA strands, identical DNA strands are normally formed of a length greater than 100 bases. In one embodiment, the strands are marked by a suitable marker at one end. The strands are divided into four aliquots and the strands within each aliquot are cleaved at any base belonging to one or more specific base types. In another embodiment, strands are synthesized to any base belonging to a specific base type. These four aliquots are then electrophoresed through one or more identical channels to separate strands so that the shorter strands are resolved towards the end of the gel prior to resolution of the longer strands, which may be near the entrance end of the gel at the time the shorter strands are being resolved. This occurs in a continuous process so a substantial number of different length strands may be resolved in a relatively short gel. This methodology takes advantage of time-resolved bands, as opposed to the limitations of spatial-resolved bands.

The gel size, electric field and DNA mobilities are such that the more mobile bands are fully resolved while the less mobile bands are yet unresolved in a continuous process such that at least ten percent of the bands have been resolved by electrophoresis in the gel while the less mobile bands which are near the entrance end of the gel are not fully resolved. These less mobile bands become resolved little by little over time in a continuous fashion without interruption of the movement of these bands through the gel. The markers are detected by transmitting infrared light to fluorescently marked DNA strands.

To obtain maximum information in those embodiments in which a gel slab is scanned, a microscope and laser are moved together on a platform with respect to the gel. To ensure parallelism between the microscope/laser assembly and the slab gel as well as optimal focusing of the assembly onto the slab gel, in one embodiment, the sensor determines the point in the glass-gel-glass sandwich having minimal fluorescence and focuses on it. This minimal fluorescence is due to the reduced fluorescence of the gel as compared to the glass. The microscope is continually moved and refocused as scanning takes place to maintain the optimum focus.

In another scanning embodiment, the microscope determines the optimal focus position at one location on the glass-gel-glass sandwich and then is moved to another location on the glass-gel-glass sandwich where an optimal focus position is determined for that location. The scanning mechanism is then pivoted so that the scanning mechanism is parallel to a line connecting the two optimal focus positions previously determined. This insures that the gel slab is in the focal plane of the microscope/laser assembly. The intensity signal received from the scanning microscope/laser assembly which indicates the presence or absence of DNA strands is directly transmitted to the intensity input of the computer monitor so that the display varies in brightness rather than providing an amplitude trace.

For purposes of focusing, either by pivoting the scanning mechanism or by adjusting the microscope at different points during a scan to follow an established line, the microscope/laser assembly moves orthogonal to the plane of the glass-gel-glass sandwich at one end of the scan in order to locate the position of lowest flourescence, which is the position of the gel slab between the two glass plates. Then it moves to the other end of its scan and performs the same function. These two focusing movements are utilized to move the scan mechanism in one embodiment and to program the movement of the microscope focus in another embodiment so that the microscope in the one embodiment moves continuously along a single line and the scan mechanism has been prepositioned such that that line is parallel to the gel slab, and in the other embodiment, the focus is changed at six points to accommodate a non-parallel alignment between the scan mechanism and the gel.

From the above summary, it can be understood that the sequencing techniques of this invention have several advantages, such as: (1) they take advantage of resolution over time, as opposed to space; (2) they are continuous; (3) they are automatic; (4) they are capable of sequencing or identifying markers in relatively long strands including strands of more than 100 bases; (5) they are relatively economical and easy to use; (6) they permit efficient focusing of a light sensor onto the DNA bands; and (7) they provide an easy to observe display.

SUMMARY OF THE DRAWINGS

The above noted and other features of the invention will be better understood from the following detailed description when considered with reference to the accompanying drawings in which:

FIG. 9 is a perspective view from the bottom right side of the sequencing system of FIG. 8;

FIG. 10 is a flow diagram of a program used to control the operation of the system of FIG. 8 and FIG. 9;

FIG. 11 is a more detailed flow diagram of the software control for a portion of the program of FIG. 10;

FIG. 12 is a schematic diagram of another portion of the program of FIG. 10;

FIG. 13 is a block diagram of another embodiment of the program of FIG. 12;

FIG. 14 is a block diagram of a control portion for the embodiments of FIGS. 1–13;

DETAILED DESCRIPTION

Figure 1:
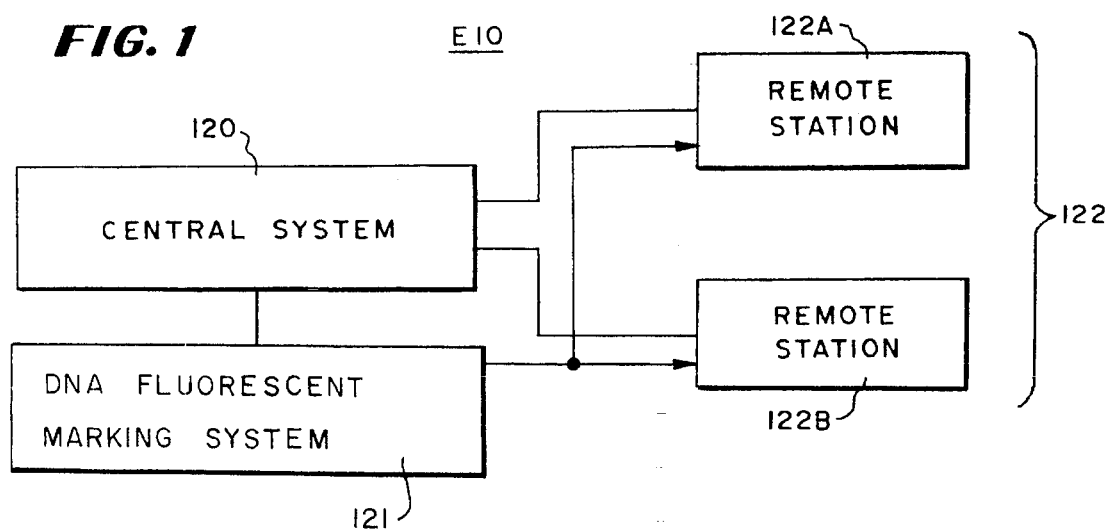
FIG. 1 is a block diagram of an embodiment of the invention.

In FIG. 1, there is shown an embodiment 10 of sequencing system having a central system 120, a plurality of remote stations, two of which are shown at 122A and 122B and a DNA fluorescent marking system 121. The DNA fluorescent marking system 121 includes means for labeling identical strands of DNA and a DNA preparation system. In this preparation process, strands are separated into four aliquots. The strands in a given aliquot are either individually cleaved at or synthesized to any base belonging to one or more of the four base types, which are adenine, guanine, cytosine and thymine (hereinafter A, G, C and T). The adenine-, guanine-, cytosine- and thymine-terminated strands are then electrophoresed for separation. The rate of electrophoresis indicates the DNA sequence.

The fluorescent markers are attached to the identical strands of more than 100 bases in a container. The flourescent markers may be attached to DNA primer molecules or to deoxynucleotide triphosphates used in the synthesis of the DNA strands or to dideoxynucleotide triphosphates which terminate synthesis of the DNA strands. Single or multiple fluorescent markers may be attached to the DNA fragments. They must be of :such a size and have such chemical characteristics as to not obscure the normal differences in the mobilities between the different fragments due to terminations at different ones of the adenine, guanine, cytosine and thymine bases and be able to be easily detected.

The DNA fluorescent marking system 121 communicates with the central system 120 as well as the remote stations 122A and 122B. The central system 120 includes a separating system and a detection and processing system to separate the strands by length with each fragment being terminated at a different one of the A, T, G and C groups. The separating system, which sequences strands by length, communicates with the detection and processing system which analyzes the fragments by comparison of the progress of each band of DNA fragments along the gel with the other bands to derive information about the sequence of the DNA.

The separating system continuously sequences strands of DNA, and for this purpose, the preferred embodiment includes at least four electrophoresis channels, each adapted to receive fluorescently labeled DNA strands having at one end a base of a given type. Each of the channels has a gel path and electrical field across it identical in its characteristics to the gel path of the other channels and electrical fields across the other channels. The bands are detected in a manner that indicates their mobility in the gel to indicate the sequence of the A, G, C and T strands of different lengths.

The detection and processing system includes a scanning apparatus having a light source, such as a laser or arc lamp or other suitable source that emits light in the optimum absorption spectrum of the marker. The light may be split by the use of fiber. In the preferred embodiment, the light source is a diode laser that irradiates the channels with infrared light having a wavelength that matches the absorbance region of the marker. The detector includes a light sensor that is preferably an avalanche photodiode that is sensitive to the near infrared light emission of the marker. It may include a filtering system having a pass band suitable for passing selectively the optimum emission of the fluorescent marker to the light sensor.

The photodiode, photomultiplier or other light detector selectively detects the fluorescence using techniques which enhance the signal/noise ratio. One technique is to modulate the laser source by pulsing the electrical current driving the laser and detect light in sequence with the emitted light by connecting the output signal from the sensor in circuit with a lock-in amplifier that is sequenced with the pulsed laser light. Another technique is the use of laser pulses which are less than five nanoseconds time duration, with detection in a time window. The length of such window and its delay from the pulse are optimized to discriminate against background fluorescence as well as scattered laser light.

To determine the sequence of strands, the processing system includes means for correlation between the channel in which the fluorescent light is detected with the time of detection and means for indicating: (1) if the type of base termination or nucleotide cleavage is A, G, C or T; and (2) the time sequence of separation of each strand in each channel of the electrophoresis gel.

To use the apparatus to sequence DNA strands, identical DNA strands are normally formed of a length greater than 100 bases. In one embodiment, the strands are marked by a suitable marker. The strands are divided into four aliquots and the strands within each aliquot are cleaved at any base belonging to a specific base type or are synthesized to any base belonging to a specific base type. These four aliquots are then electrophoresed through identical channels to separate strands so that the shorter strands are resolved towards the end of the gel prior to resolution of the longer strands, which still are near the entrance end of the gel. In another embodiment, the strands are divided into four aliquots and cleaved or synthesized to a given base before being marked. The same marker may be used for all four aliquots and separation may be performed as described above or a different marker may be used for each different termination group of the A, T, C and G groups so as to process in a single channel for a complete sequence. This occurs in a continuous process so a substantial number of different length strands may be resolved in a relatively short gel. This methodology takes advantage of time-resolved bands, as opposed to the limitations of spatial-resolved bands.

The gel size, electric field and DNA mobilities are such that the more mobile bands are fully resolved while the less mobile bands are yet unresolved in a continuous process such that at least ten percent of the bands have been resolved by electrophoresis in the gel while the less mobile bands which are near the entrance end of the gel are not fully resolved. These less mobile bands become resolved little by little over time in a continuous fashion without interruption of the movement of these bands through the gel. The markers are detected by transmitting infrared light to fluorescently marked DNA strands which may be at the same infrared wavelength or at four different infrared wavelengths depending on the embodiment of separation technique.

The remote stations 122A and 122B each are able to perform the sequencing but some portions of data processing can only be performed by the central station 120. It may supply data to the remote stations, such as 122A and 122B, to which it is electrically connected and receive data from them. With this arrangement, the central sequencing system 120 may cooperate with one or more of the remote stations, such as 122A and 122B, for increased capability such as increased number of channels. Each unit may control the parameters used in sequencing, such as the electrophoresis potential or the like.

Figure 2:
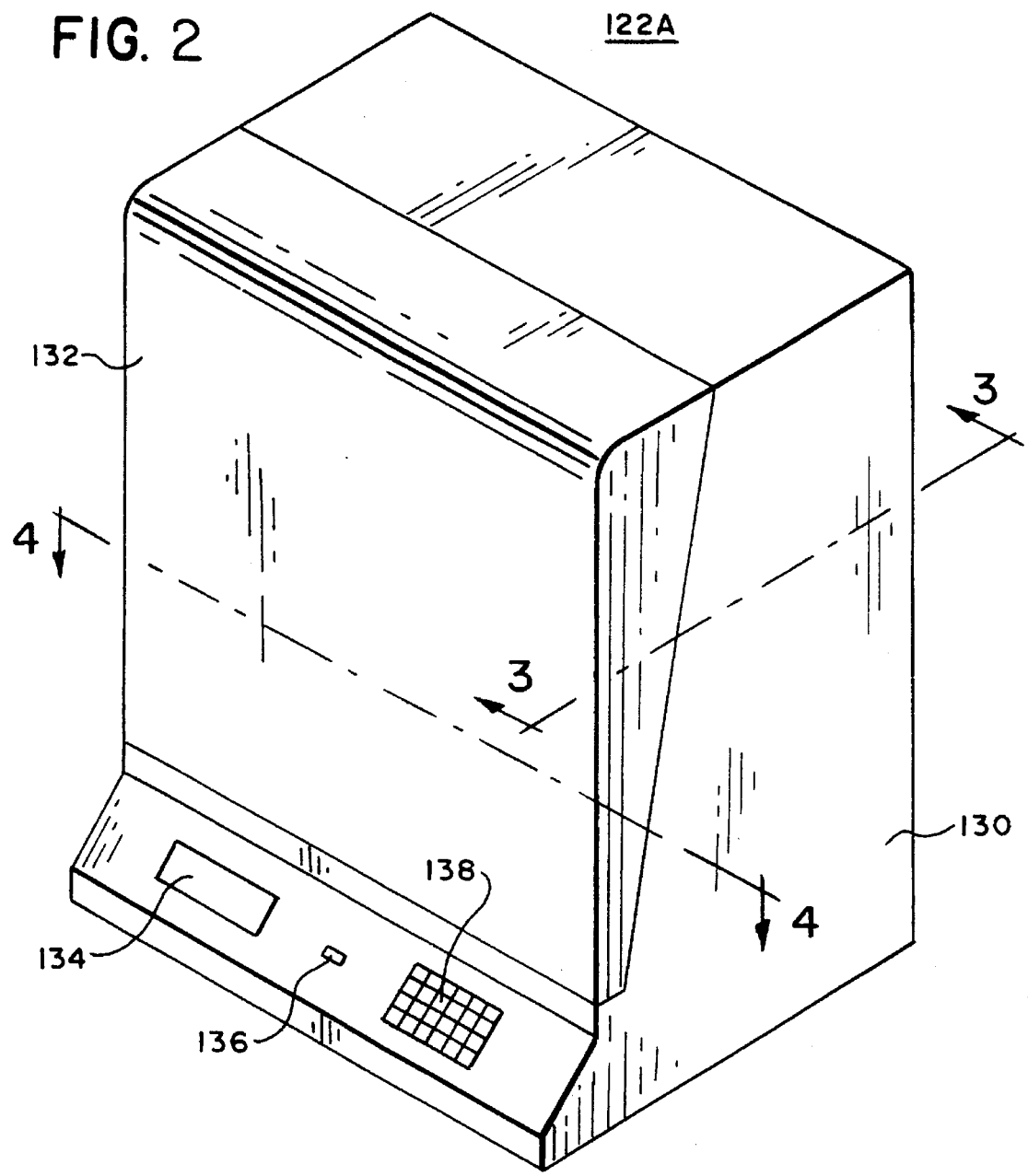
FIG. 2 is a perspective view of a portion of the embodiment of FIG. 1.

In FIG. 2, there is shown a simplified view of the remote station 122A having a cabinet housing 130, a front cover 132, a liquid crystal display readout 134, a high voltage warning light 136 and a plurality of function keys 138. In FIG. 2, the remote station 122A is shown closed. However, the front cover 132 may be removed to expose an electrophoresis section. The potential applied across the gel may be set and different data readouts may be selected either from the analysis provided within the central system 120 (FIG. 1)

or values from within the remote station 122A using the function key pad 138 and the selected data displayed on the liquid crystal display readout 134 prior to and/or after selection.

Figure 3:
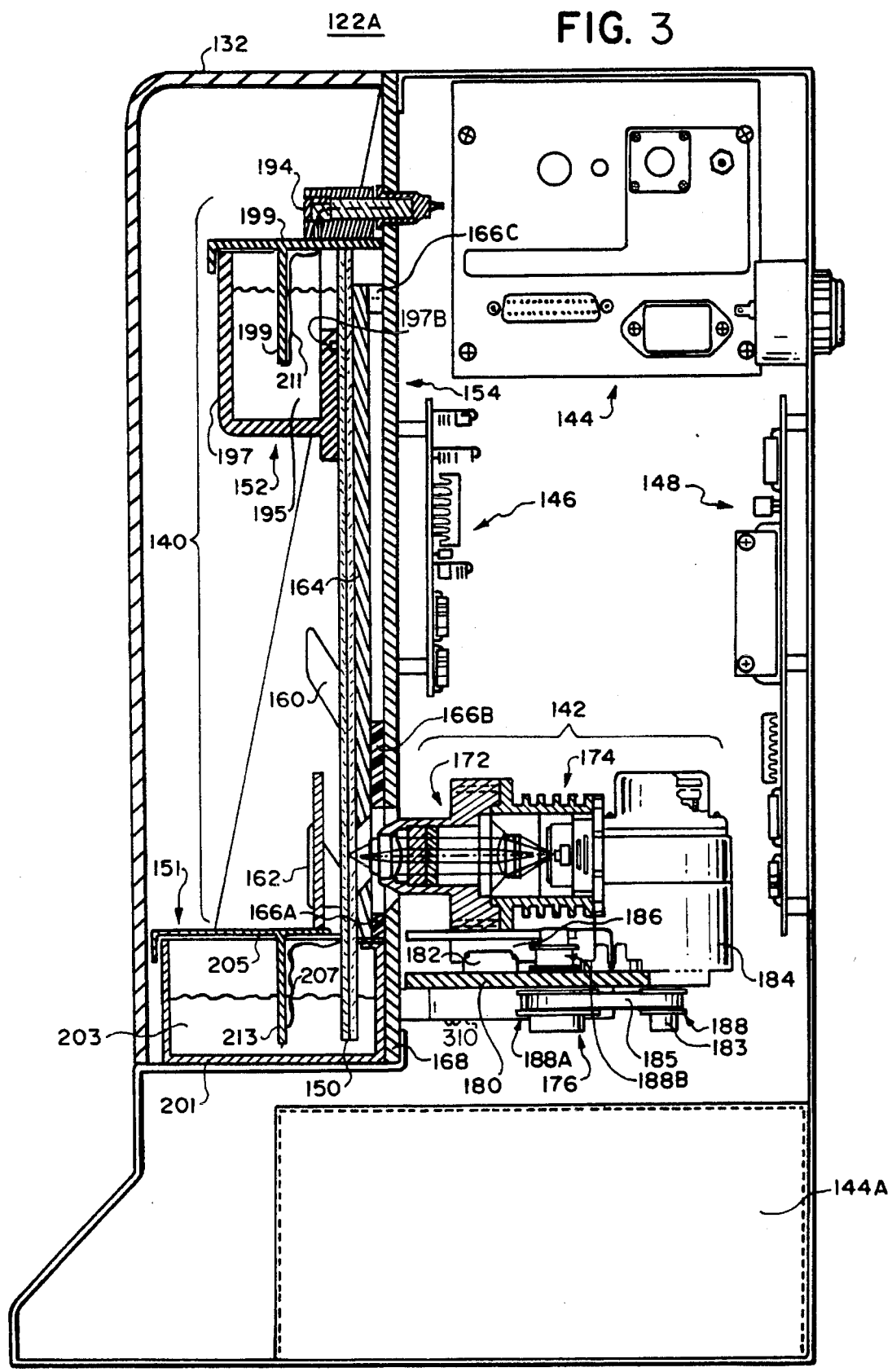
FIG. 3 is a sectional view taken through lines 3—3 of FIG. 2.

In FIG. 3, there is shown a sectional view of a portion of the remote station 122A taken through section lines 3—3 of FIG. 2 having an electrophoresis section 140, a scanning section 142, an electrophoresis power supply 144, a system power supply section 144A, an analog board 146 and a digital board 148. The electrophoresis section 140 is positioned near the front of the cabinet and a portion of it is adapted to be scanned by the scanning section 142 in cooperation with circuitry on the analog board 146 and the digital board 148. All of the apparatus are electrically connected to the power supply section 144A for such operation.

To separate different DNA fragments into bands, the electrophoresis section 140 includes a gel sandwich 150, an upper buffer assembly 152, a support assembly 154, and a lower buffer assembly 151 positioned to enclose the bottom of the gel sandwich 150. In the embodiment of FIG. 3, the gel sandwich 150 is held substantially vertically and its temperature is controlled during operation. Bands are separated by applying voltage to the upper buffer assembly 152 and lower buffer assembly 151 and scanned by the scanning section 142.

To support the gel sandwich 150, the support assembly 154 includes a pair of upper side brackets and lower side brackets 160 and 162 (only one of each pair being shown in FIG. 3), an apparatus support plate 168, a temperature control heating plate 164 and a plastic spacer, shown at 166A–166C, in FIG. 3. The entire structure is supported on the apparatus support plate 168 which mounts the upper and lower side brackets 160 and 162.

The upper and lower side brackets 160 and 162 are each shaped to receive a pin such as 161 and 167 (FIG. 6) extending from a gel sandwich such as the gel sandwich 150 and thus hold the gel sandwich in place on one side in juxtaposition with the scanning section 142. The pin 167 (FIG. 6) on the side of the sandwich opposite to the pin 161 (FIG. 6) fits into a corresponding one of two brackets 163 and 160 (FIG. 6) so that the gel sandwich can be hooked in place. The other two brackets 165 and 162 are positioned to receive the pins of other length gel sandwiches with the lower bracket 162 receiving pins of shorter vertical length sandwiches than the upper bracket 160. Even longer gel sandwiches can be mounted by substituting a longer heating plate for the heating plate shown at 164.

The spacer as shown as 166A–166C space the temperature control heating plate 164 from the apparatus support plate 168 and maintain it at a constant selected temperature above ambient temperature. In the preferred embodiment, the temperature is maintained at 50 degrees Centigrade and should be maintained in a range of 30 degrees to 80 degrees.

The scanning section 142 includes a laser diode assembly (not shown in FIG. 3), a microscope assembly 172, a photodiode section 174 and a scanner mounting section 176. The laser diode assembly (not shown in FIG. 3) is positioned at an angle to an opening in the apparatus support plate 168 and the heating plate 164 so that light impinges on the gel sandwich 150 to cause fluorescence with minimum reflection back through the microscope assembly 172.

To receive the fluorescent light, the microscope assembly 172 is focused on the gel sandwich 150 and transmits fluorescent light emitted therefrom into the photodiode section 174 which converts it to electrical signals for transmission to and processing by the analog and digital boards 146 and 148 which may provide further analysis of data. The scanning section 142 moves along a slot in the apparatus support plate 168 which is mounted to the scanner mounting section 176 during this operation in order to scan across the columns in the gel sandwich 150.

The scanner mounting section 176 includes a mounting plate 180, a bearing 182, a stepping motor 184, a slidable support 186 and a belt and pully arrangement 185, 188A and 188B. The mounting plate 180 is movably mounted to the appartus support plate 168 through a frame member and supports the elongated bearing plate 182, the stepping motor 184 and two pulleys 188A and 188B. The elongated bearing plate 182 extends the length of the gel sandwich 150.

To permit motion of the laser diode assembly (not shown) and microscope assembly 172 with respect to the gel sandwich 150, the slidable support 186 supports the microscope assembly 172 and diode assembly and slidably rests upon the bearing plate 182. An output shaft 183 of the stepping motor 184 drives a pulley 188B through pulley 188, belt 185, and pulley 188A and the pulley 188B drives a belt (not shown) that is clamped to the slidable support 186 to move it the length of the gel sandwich 150 during scanning by the laser diode and microscope assembly 172 which rest upon it. The stepping motor 184 under the control of circuitry in the digital board 148 moves the pulley 188B to move the belt (not shown) and thus cause scanning across the gel sandwich 150.

As shown in this view, the electrophoresis power supply 144 is electrically connected to buffer in the upper buffer assembly 152 through an electrical connector 194 and to the lower buffer assembly 151 through a connector not shown in FIG. 3.

The upper buffer assembly 152 includes walls 197 forming a container to hold a buffer solution 195 and a cover 199 formed with a lip to fit over the walls 197 from the top and containing a downwardly extending flat member spaced away from the side walls and holding a conductor 211. The conductor 211 is electrically connected to the source of power through connector 194 which is mounted to the top of the cover 199 to permit electrical energization of the buffer solution 195.

The bottom buffer assembly 151 includes enclosed walls 201 defining a container for holding a buffer solution 203 and a cover 205 closing the container 201 and having a downwardly extending portion 213 extending into the buffer solution 203 for supporting a conductor 207 for applying energy to the bottom buffer solution 203. The gel sandwich 150 extends downwardly into the buffer solution 203 and upwardly into the buffer solution 195 to permit the electrical contact for electrophoresis. An "O" ring 197B provides a seal for the upper buffer assembly 152 so that the buffer solution 195 does not empty out of the upper buffer assembly 152.

Figure 4:
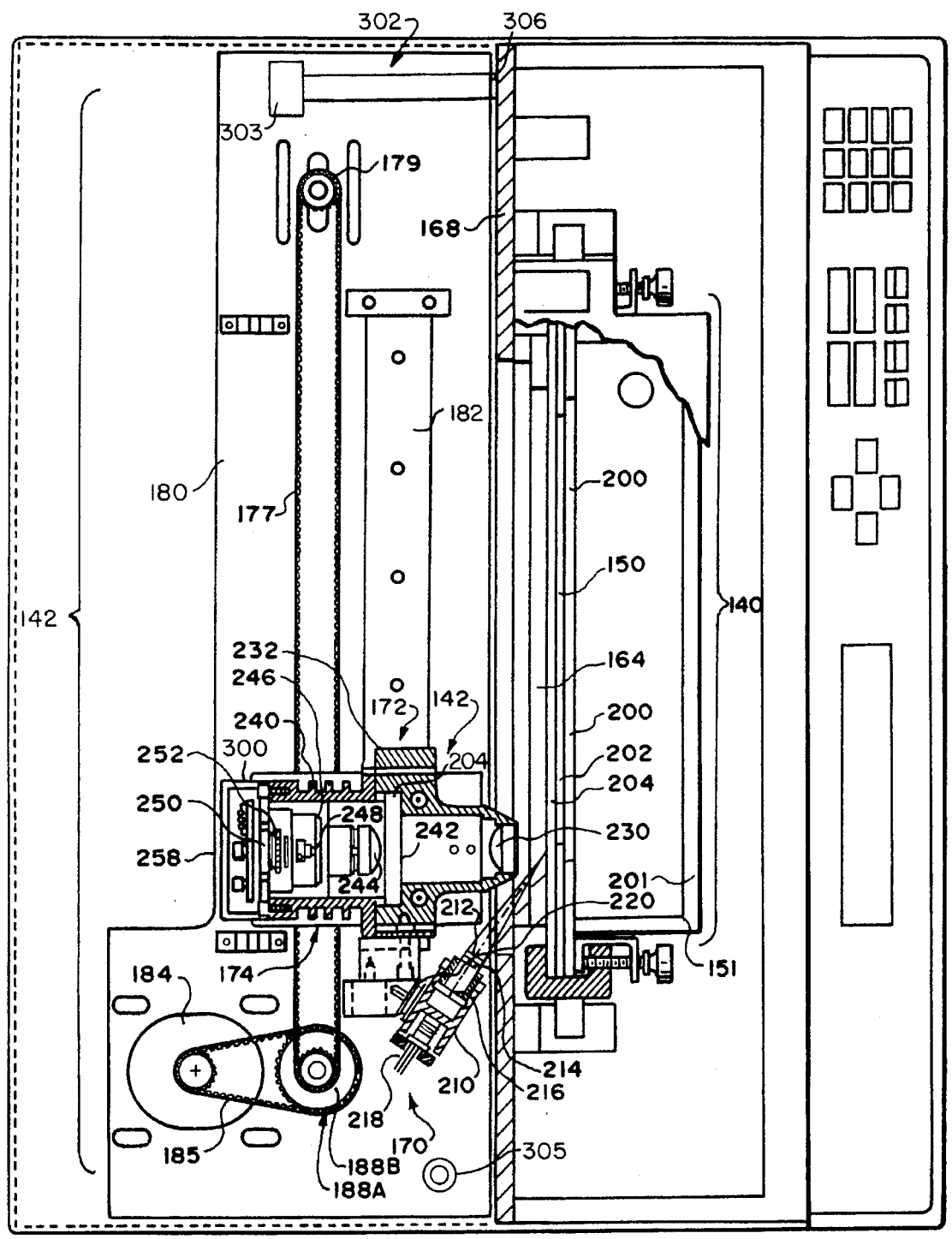
FIG. 4 is a sectional view of a portion of FIG. 2 taken through lines 4—4.

In FIG. 4, there is shown a sectional view taken through lines 4—4 of FIG. 2 showing a portion of the electrophoresis section 140, a portion of the scanning section 142 (indicated twice in FIG. 4 for clarity) and the electrophoresis power supply section 144A (FIG. 3) mounted together to illustrate from a top view the arrangement of the apparatus support plate 168, the heater plate 164, the gel sandwich 150, a laser diode assembly 170, a microscope assembly 172 and a photodiode assembly 174. The heater plate 164 and apparatus support plate 168 have slots running in a horizontal direction orthogonal to the lanes of DNA in the electrophoresis section 140 sized to receive the ends of a laser diode assembly 170 and the microscope assembly 172 for scanning thereof.

To cooperate with the separation and scanning of DNA bands, the gel sandwich 150 includes a front glass plate 200, a gel section 202 and a rear glass plate 204 mounted in contact with the heater plate 164 and having a section exposed for scanning by the laser diode assembly 170 and the microscope assembly 172. The rear glass plate 204 contacts the heater plate 164 and is separated from the front glass plate 200 by the gel section 202 within which DNA separation takes place. The front and rear glass plates 200 and 204 may be any type of glass but are preferably soda lime which has low fluorescence in the infrared and near infrared regions and is prepared by a process that provides optically flat surfaces without grinding.

To transmit light to the gel sandwich 150, the laser diode assembly 170 includes a housing 210, a focusing lens 212, a narrow band pass filter 214, a collimating lens 216 and a laser diode 218. The laser diode 218 emits infrared or near infrared light which is collimated by the laser collimating lens 216 and filtered through the narrow band pass infrared filter 214. This light is focused by the focusing lens 212 onto the gel sandwich 150. Preferably, the point of focus on the gel section 202 of the gel sandwich 150 lies along or near the central longitudinal axis of the microscope assembly 172 and the photodiode assembly 174.

The thickness of the glass plates and the gel, the position of the laser and microscope assembly and thus the angle of incidence and angle of reflection of the light from the laser and to the microscope assembly are chosen, taking into consideration the refractive index of the gel and glass and the thickness of the glass plates and the gel, so that the light from the laser is maximally transmitted to the gel. The light from the laser is not directly reflected back because the angle of incidence to a normal is equal to the Brewster's angle at the first interface and is such as to impinge on the markers with full intensity after refraction but not be reflected by the first surface of the gel sandwich 150 into the microscope assembly and the microscope assembly views those markers that fluoresce in its line of sight.

To maintain temperature control over the laser diode, the housing 210: (a) is coupled to a heat sink through a thermal electric cooler 220, and (b) encloses the focusing lens 212, narrow band pass filter 214, collimating lens 216 and laser diode 218; and (c) accommodates the electrical leads for the diode.

To receive and focus light emitted by fluorescent markers from the gel section 202 in response to the light from the laser diode assembly 170, the microscope assembly 172 includes a collection lens 230, a housing 232, and a focusing motor. The microscope assembly 172 is adapted to be positioned with its longitudinal axis centered on the collection lens 230 and aligned with the photodiode assembly 174 to which it is connected. For this purpose, the housing 232 includes a central passageway in which are located one or more optical filters (not shown) with a pass band matching the emission fluorescence of the marked DNA strands. With this arrangement, the collection lens 230 receives light from the fluorescent material within the gel section 202 and collimates the collected light for optical filtering and then transmission to the photodiode assembly 174.

To generate electrical signals representing the detected fluorescence, the photodiode assembly 174 includes a housing 240 having within it, as the principal elements of the light sensors, an inlet window 242, a focusing lens 244, a sapphire window 246 and an avalanche photodiode 248. To support the avalanche photodiode 248, a detector mounting plate 250 is mounted within the housing 240 to support a plate upon which the avalanche photodiode 248 is mounted. The inlet window 242 fits within the housing 240 to receive light along the longitudinal axis of the photodiode assembly 174 from the microscope assembly 172.

Within the housing 240 of the photodiode assembly 174, the sapphire window 246 and avalanche photodiode 248 are aligned along the common axis of the microscope assembly 172 and the photodiode assembly 174 and focuses light transmitted by the microscope assembly 172 onto a small spot on the avalanche photodiode 248 for conversion to electrical signals. A thermoelectric cooler 252 utilizing the Peltier effect is mounted adjacent to the detector mounting plate 250 to maintain a relatively cool temperature suitable for proper operation of the avalanche photodiode 248.

As best shown in this view, the stepping motor 184 rotates the belt 185 to turn the pulley 188A, which, in turn, rotates pulley 188B. The pulley 188B includes a belt 177 extending between it and an idler pulley 179 and is attached at one location to the slideable support 186 (FIG. 3) to move the scanning microscope and laser lengthwise along the gel sandwich 150 for scanning purposes. The motor 184, by moving the carriage back and forth accomplishes scanning of the gel sandwich 150.

Figure 5:
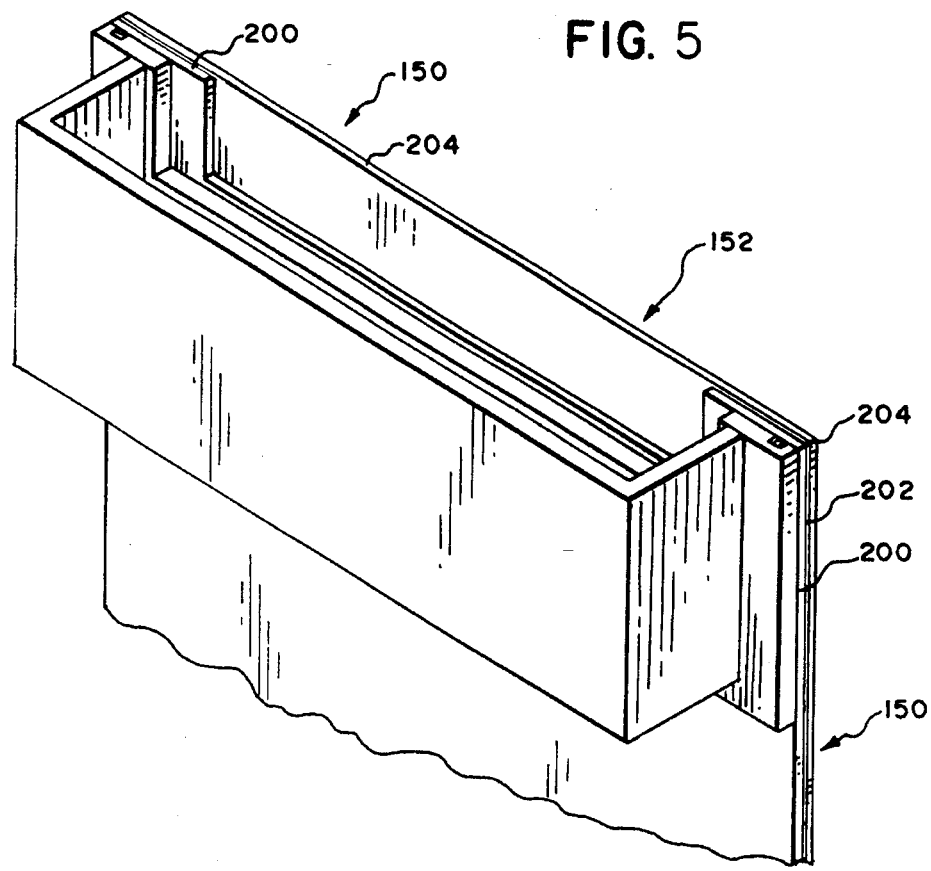
FIG. 5 is an exploded perspective view of a portion of the embodiment of FIG. 4.

In FIG. 5, there is shown a fragmentary perspective view of the gel sandwich 150 and the upper buffer assembly 152 mounted to each other showing the outer glass plate 200 cut away from the rear glass plate 204 to expose the gel section 202 to buffer solution within the upper buffer assembly 152. With this arrangement, DNA samples may be pipetted between the glass plates 200 and 204 and moved downwardly by electrophoresis beyond the upper buffer assembly 152 and through the gel sandwich 150 to the bottom buffer (not shown in FIG. 5).

Figure 6:
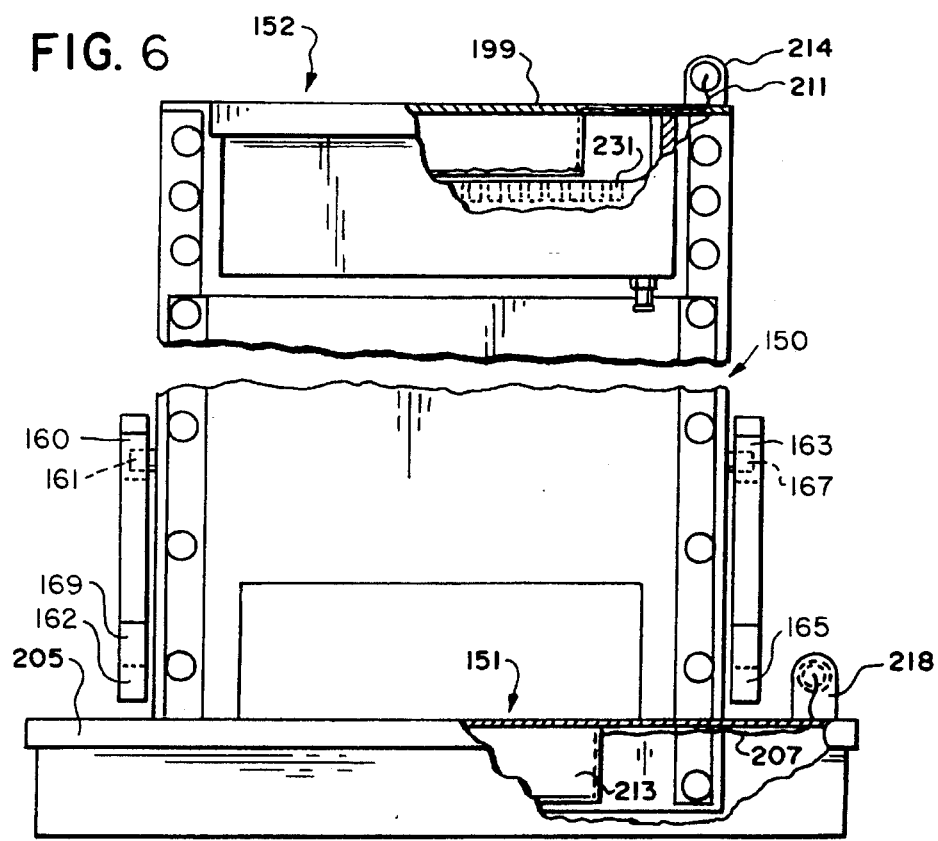
FIG. 6 is an enlarged view, partly broken away, of a portion of the embodiment of FIG. 4.

In FIG. 6, there is shown a broken away view of the gel sandwich 150 illustrating the upper buffer assembly 152 and the lower buffer assembly 151 connected to it at each end. As shown in this view, the cover 199 includes a connecting post 214 which receives the elongated flexible conductor 211 for connection to the downwardly extending portion of the cover 199 into the buffer compartment. This flexible conductor has sufficient length to accommodate different lengths of gel sandwiches that cause the upper buffer assembly 152 to be at different elevations. In another embodiment, the length of conductor 211 is the same for the different lengths of gel sandwiches in that this cover 199 is raised or lowered depending on the gel length. To accomodate electrical connection in this embodiment, either the connecting post 214 mates with one of a series of mounting connectors located at different vertical positions on the apparatus support plate 168 (FIG. 3) or the connecting post 214 mates with a flexible extension cable that electrically connects the connecting post 214 with a mounting connector.

As best shown in this view, a plurality of side brackets 160, 163, 165 and 169 are mounted to the apparatus support plate 168 (FIG. 3) to receive pins 161 and 167 extending from the sides of the gel sandwich 150 to support the gel sandwich in place. The pins 161 and 167 extend from opposite sides of the gel sandwich at the same elevation and the brackets 160, 163, 165 and 169 are mounted in pairs to the apparatus support plate 168 (FIG. 3) with each pair being at a different elevation and each bracket of a pair of brackets being positioned on the opposite side of the gel sandwich from the other bracket of the same pair to support different sizes of gel sandwichs at a location that provides balance to them.

The upper and lower side brackets 160 and 162 on one side of the gel sandwich and the upper and lower side brackets 163 and 165 on the opposite side are each shaped to receive a pin such as 161 and 167 (FIG. 6) extending from the gel sandwich 150 and thus hold the gel sandwich in place on one side in juxtaposition with the scanning section 142 (FIGS. 3 and 4). The pin 167 on the side of the sandwich opposite to the pin 161 fits into a corresponding one of the two brackets 163 and 165 so that the gel sandwich can be hooked in place. For longer gel sandwiches, the pin 167 fits into bracket 163 while for shorter gel sandwiches the pin 167 fits into bracket 165. The other of the two brackets 160 and 169 are positioned to receive the pin located on the opposite side of the gel sandwich such that the lower bracket 169 receives the pin of shorter vertical length gel sandwiches and the upper bracket 160 receives the pin of longer vertical length gel sandwiches. Even longer gel sandwiches can be mounted by substituting a longer heater plate for the heater plate shown at 164 (FIG. 3). As best shown in this view, recesses 231 extend downwardly into the gel to receive DNA sample from a pipette and thus form channels for electrophoresing.

To form an electical connection through the gel sandwich 150 from the upper buffer assembly 152 to the lower buffer assembly 151, a conducting post 218 is connected to the cover 205 of the lower buffer assembly 151 for receiving the conductor 207 (FIG. 3) which extends downwardly to the downwardly extended plate 213 and into the buffer solution.

Figure 7:
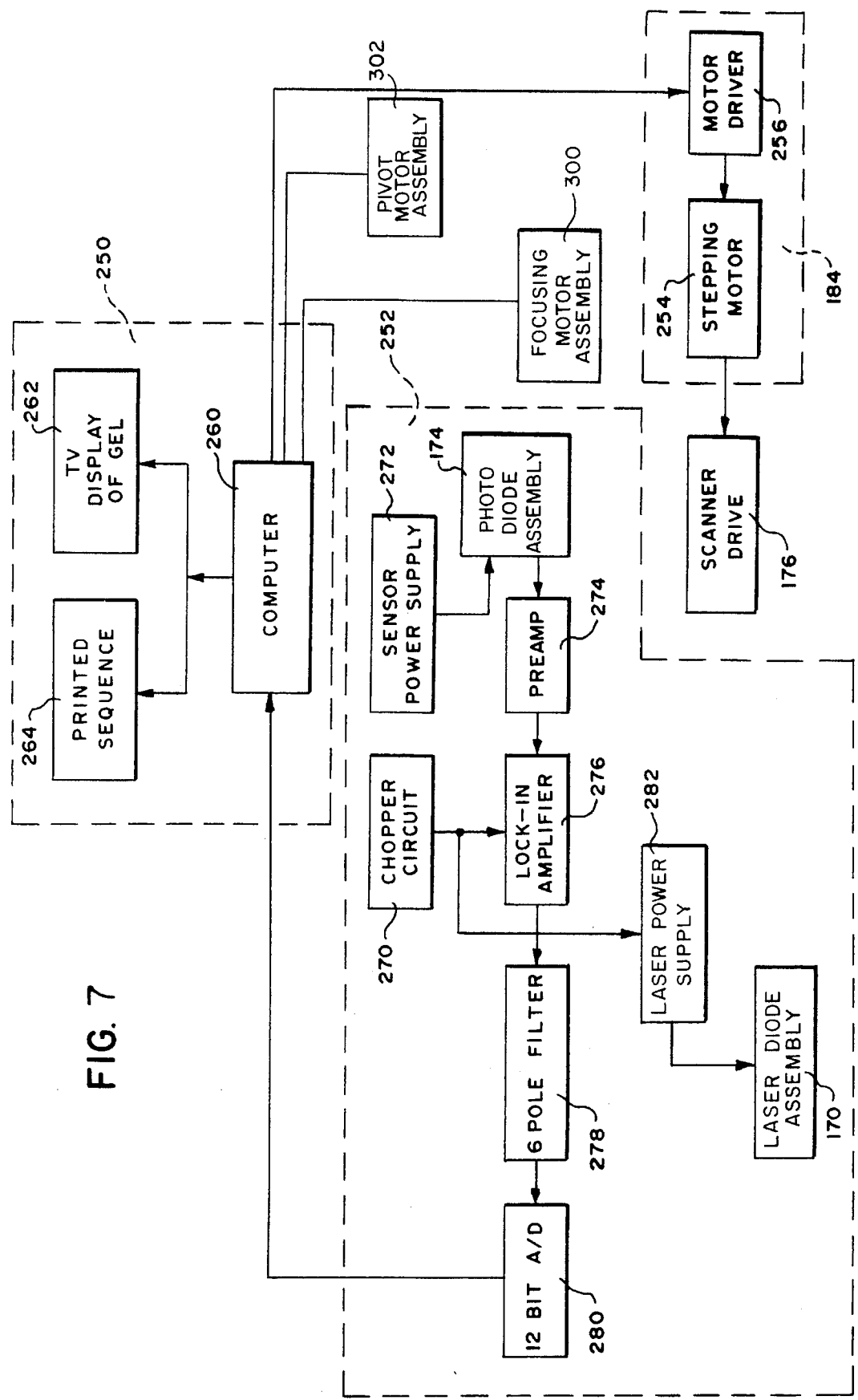
FIG. 7 is a block diagram of a circuit that may be used for coordination of a sensor, scanner drive and laser used in the embodiment of FIG. 9.

In FIG. 7, there is shown a block diagram of the circuitry used to control the remote station 122A of the embodiment of FIG. 2 having a control, correlation and readout section 250, a scanner drive 176, the motor assembly 184 for moving the scanner drive 176, the sensing configuration 252 and the focusing motor assembly and pivot motor assemby controls 300 and 302 respectively.

The sensing configuration 252 includes the laser diode assembly 170 and the photodiode assembly 174 which receives signals, removes some noise, and transmits the signals for display and read out in the control, correlation and read out section 250. At the same time, the scanner drive 176 and motor for the scanner drive 184 receive signals from the control, correlation and readout section 250 to control the motion of the sensor back and forth across the gel sandwich. This overall configuration is not part of the invention of this application except insofar as it cooperates with the sensing configuration 252 to scan the DNA and determine its sequence in accordance with the embodiments of FIGS. 1–6.

To drive the laser diode assembly 170 and the microscope assembly 172 (FIGS. 3 & 4) and the photodiode assembly 174 from position to position, the motor assembly 184 includes a stepping motor 254 and a motor driver 256. The motor drive 256 receives signals from the control correlation and readout section 250 and actuates the stepping motor 254 to drive the scanner drive 176. The scanner drive 176 is mechanically coupled to the stepping motor 254 through a belt and pulley arrangement for movement back and forth to irradiate and sense the electrophoresis channels on the gel sandwich 150 (FIG. 3). The stepping motor 254 and motor driver 256 are conventional and not themselves part of the invention.

To correlate the scan with received signals and provide a display of them, the control, correlation and readout system 250 includes a computer 260 which may be any standard microprocessor, a television display or cathode ray tube display 262 and a printer 264 for displaying and printing the results of the scans. Data, after being processed in sensing configuration 252 is supplied to the computer 260 for correlation with the position of the scanner drive 176 as controlled by the computer 260 and display 262.

To sense data, the sensing configuration 252 includes in addition to the laser diode assembly 170 and the photodiode assembly 174, a chopper circuit 270, a sensor power supply 272, a preamplifier 274, a lock-in amplifier 276, a 6-pole filter 278, a 12-bit analogue digital converter interface circuit 280 and a laser power supply 282. The photodiode assembly 174 receives light from the laser diode assembly 170 after it impinges upon the gel sandwich 150 (FIG. 3) and transmits electrical signals through preamplifier 274 to the lock-in amplifier 276. The photodiode assembly 174 receives signals from the sensor power supply 272. The chopper circuit 270 provides pulses at synchronized frequencies to the lock-in amplifier 276.

The laser diode assembly 170 receives power from the power supply 282 which is controlled by the chopper circuit 270 so that the signal from the laser diode assembly 170 is in synchronism with the signal applied to the lock-in amplifier 276 so that the output from the lock-in amplifier 276 to the 6-pole filter 278 discriminates against unwanted signal frequencies. This signal is converted to a digital signal in the 12-bit analogue to digital converter 280 which serves as an interface to the computer 260.

Figure 8:
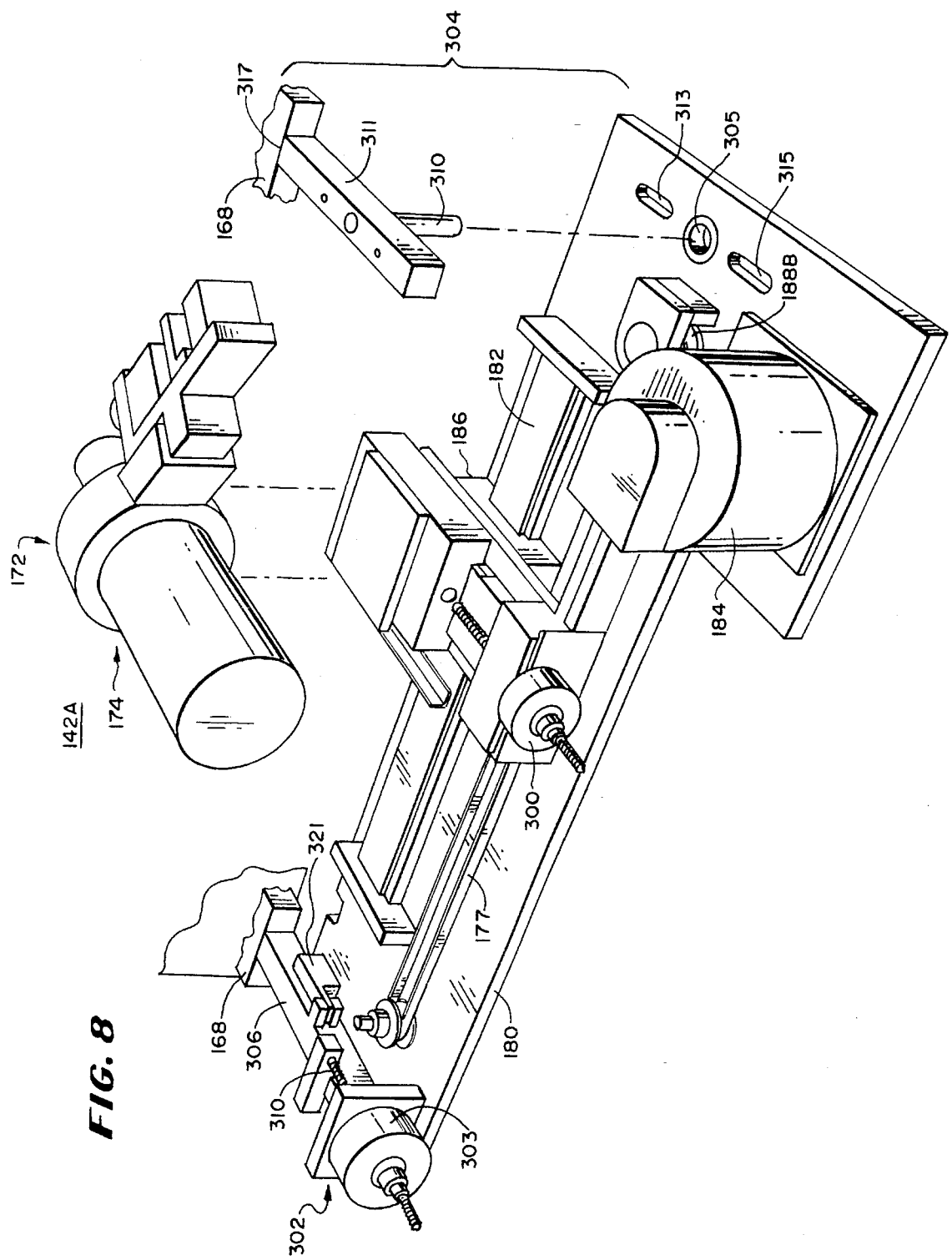
FIG. 8 is a perspective view from the top right side of another embodiment of scanning section usable in the DNA sequencing apparatus of FIGS. 1 and 2.

To maintain optical focus, the computer 260 is electrically connected to the pivot motor assembly 302 and the focusing motor assembly 300, which motor assemblies are able to adjust the microscope assembly 172 (FIGS. 3 and 4) to focus it and to adjust the location of the microscope with respect to the gel sandwich 150 by pivoting the support bed 180 (FIGS. 4 and 8). As will be better explained hereinafter, this permits a number of different focusing arrangements such as one in which the microscope is periodically refocused during an individual scan across the gel to maintain focus and one in which the distance between the gel sandwich and the path of travel of the microscope is adjusted with respect to each other so that during movement of the microscope as it scans, the focal point is maintained on the gel even though there was originally some non parallelism between the gel and the travel path of the microscope along the course of a scan. Of course both motors may be controlled simultaneously as better explained hereinafter.

In FIG. 8, there is shown a fragmentary, exploded top perspective view of another embodiment of scanning section 142A substantially the same as the scanning section 142 of FIGS. 3 and 4 in which the identical parts are indicated by the same reference numerals in each embodiment. As shown in this view, the scanning section 142A includes three motor assemblies, the stepping motor assembly (scan motor assembly) 184, the focusing motor 300 and a mounting plate pivot motor assembly 302 and a pivot assembly 304. The mounting plate pivot motor assembly 302 is only in the embodiment of scanning assembly 142A but the focusing motor 300 and stepping motor assembly 184 are in both the embodiment of scanning section 142 and the embodiment 142A. The motor assembly 184 operates in the same manner in both embodiments to drive the output shaft 183 (FIGS. 3 and 9) which in turn drives the slidable support 186 (FIG. 3) on the bearing plate 182 (FIGS. 3 & 4) through the belt 185 (FIGS. 3 & 9) and toothed belt 177.

The focusing motor assembly 300 is mounted for movement with the microscope assembly 172 and photodiode assembly 174 to focus the microscope assembly 172 directly into the gel to receive light directly from the fluorescent markers therein. This focusing may be done manually or automatically by focusing at points where there is no fluorescent emission from DNA markers in the gel. This is done by sensing the fluorescence of the two glass plates which have relatively high emission and causing the focusing to be between the two high emission glass plates and within the lower emission gel.

The pivot motor assembly 302 cooperates with the pivot assembly 304 to adjust the angle between the gel sandwich 150 (FIG. 3) and the mounting plate 180 so that the focus of the microscope assembly 172 can be set and the focal point remain within the gel section as the microscope assembly 172 moves in a horizontal scanning direction across the gel sandwich 150 (FIG. 3). The pivot motor assembly 302 cooperates in the focusing operation so that the microscope is focused at one point at one end of the gel sandwich 150 and then the microscope assembly 172 scans across to another widely separated point without changing the focus of the microscope lens.

After the microscope assembly 172 has moved to a new location, the pivot motor assembly 302 then moves the support bed 180 about the pivot point 305 with the motion being in a horizontal plane to adjust the angle in the vertical plane of the support bed 180 and gel sandwich 150 with respect to each other so that the plane of the gel sandwich 150 and the scan direction are parallel. The focus motor 300 then refocuses the microscope assembly 172 so that the focus point is the same at both extremes of a scan, thus permitting a continuous scan without the need to dynamically refocus the microscope. Of course either the gel sandwich or support for the microscope or both can be adjusted with minor modification of the equipment.

To permit adjustment of the horizontal scanning path of the microscope assembly 172, the pivot assembly 304 in the preferred embodiment includes an opening or eyelet at pivot point 305 with the pivot point 305 having a vertical axis perpendicular to the support plate 180, a cylindrical vertically oriented pivot pin 310 and a mounting housing 311 rigidly mounted to the pivot pin 310. The pivot pin 310 fits rotatably within the support bed 180 and the support bed 180 is movably bolted to the housing 311. The bolts (not shown in FIG. 8) have shanks that extend loosely through the openings 313 and 315 to permit movement between the support plate 180 and housing 311 to permit pivoting of the support bed 180 with respect to the housing 311. The housing 311, which is mounted at end 317, and the corresponding end of a support member 306 are mounted to the apparatus support plate 168 (FIG. 3) to movably support the two ends of the support bed 180 on the DNA sequencer frame.

To provide pivoting, the pivot motor assembly 302 includes the motor output shaft 319, biasing member 321 and support member 306 so that rotation of the motor 303 in one direction causes the motor output shaft 319 to push against the vertical apparatus support plate 168 (FIG. 3) to which it is movably mounted at one end to increase the angle, and rotation in the other direction pulls it to reduce the angle or releases it to be pulled by a biasing member 321 to move the bed forwardly to the plate 168 and decrease the angle. The support member 306 is mounted to the support plate 180 by bolts (not shown in FIG. 8) having their shanks fitting through slots similar to 313 and 315 that are large enough to permit pivoting. The support member 306 is mounted to vertical apparatus support plate 168 so that the support member 306 is supported to the frame of the DNA sequencer.

In FIG. 9, there is shown a bottom perspective view of the support plate 180 showing a mounting support means 308, shaft 183, pivot hole 305 and bolt holes 313 and 315, the motor assembly 184, the pivot and the pivot motor assembly 302 illustrating the manner in which the pivot pin is mounted to the frame to permit movement of the support plate 180 by the pivot motor assembly 302.

In the embodiment of FIGS. 8 and 9 the angle of the support plate 180 is changed to cause the microscope to remain focused during a scan. In another embodiment, the angle of the support plate 180 is not changed but the microscope is refocused at a number of points during a horizontal scan to maintain the focus point within the gel. This method has certain inertia problems which slow down the scan or decrease its precision because of the larger number of times the assembly must start or stop.

In FIG. 10, there is shown a general block diagram 320 of a control program permitting the computer to control the focusing of the microscope during a scan so that the focal point remains within the gel of the gel sandwich. This program includes the general step 322 of obtaining focus points such as a single right and left point or a number of points and the step 324 of adjusting for scan depth and performing the scan.

In one embodiment, the focus points are in the gel away from the channels having DNA bands on both the right and left side of a horizontal scan and in another embodiment, it is at a plurality of points along a scan between channels having bands as well as near the ends of the scans. In another embodiment, the focusing is performed prior to the DNA bands being electrophoresced so that it is not necessary to select particular scan locations for the purpose of avoiding such DNA bands. In the former embodiment, the microscope is focused within the gel at one side, in which side there is the pivot point 305 (FIG. 8) in the scan support plate 180, and then at the second point. The microscope is moved to the second point without changing the scan. When the microscope is at the second point, the support plate 180 is moved so that, without adjusting the microscope further, the gel sandwich and support bed are altered in a parallel position. Then the microscope is refocused such that the focal point is within the gel for both locations, thus enabling a continuous scan thereafter which can proceed without dynamic focusing.

In the latter embodiment, as a scan is performed, the microscope assembly 172 refocuses at a number of points, preferably refocusing the lens by means of the focusing motor assembly, although the focusing could be done by adjusting the position of the support bed and gel sandwich with respect to each other or both focusing the lens and the position of the support bed and gel plate with respect to each other.

In FIG. 11, there is shown a block diagram of a subsequence of substeps within the step 322 for obtaining reference focal points including: (1) the substep 324 of beginning the program; (2) the substep 326 of moving the microscope to the left side of the apparatus (the zero position) and turning the laser on; (3) the substep 328 of backing the focus motor up 0.008 inches in 16 motor steps (the distance from microscope to gel is now 0.008 inches beyond the starting point at the gel sandwich); (4) the substep 330 of causing the focusing motor assembly to move forward one step, measuring the image signal one hundred times and obtaining the average of it; (5) the substep 332 of counting the steps the motor moves forward; (6) the substep 333 of deciding whether the count equals 32 motions forward or not, returning to the step 330 if it does not and if it does, the decision 332 to move to step 334; (7) the substep 334 of causing the focus motor to move back to its starting point; (8) the substep 336 of moving to a new position on the other side of the apparatus (right side in the preferred embodiment) at specified points such as one inch increments up to six inches along the scan and repeating steps 330 through 336 for each incremental location; and (9) followed by the decision step 336 of moving the scan back to its original zero point at end step 339.

With this arrangement, the microscope is moved to a starting point and focused at a number of locations for that particular starting point, such locations including the gel within them as well as portions of the glass supporting plates. Data is taken at each location a multiple number of times and averaged for precision, with this data being stored. The microscope is then moved in a horizontal scan operation to another point and the process repeated so that at least two data points are obtained and stored in the memory of the computer. These data points permit the position of the microscope and gel to be adjusted with respect to each other to maintain focus between them. It may be necessary to calculate the amount of pivoting of the microscope support and gel about a pivot point if a measurement is not directly at the pivot point.

In FIG. 12, there is shown a block diagram illustrating a subsequence within the step 324 (FIG. 10) of adjusting for scan depth and performing a scan including: (1) the substep 340 of determining where the minimum light omission occurred at different points; (2) the substep 342 of having the focus and pivot points moved so that the microscope is focused at the minimum fluorescent point at all of the locations; (3) the substep 344 of turning off the laser, moving the microscope to the zero position and resuming scanning with the laser turned back on if desired; and (4) the substep 346 of terminating the scan.

In FIG. 13, there is shown a block diagram of a program 350 illustrating a dynamic mode of scanning including: (1) the substep 352 of determining the minimum reading locations for left and right sides; (2) the substep 354 of determining the position along an equidistant straight line for at least eight points; (3) the substep 356 of moving the microscope to the zero position; (4) followed by the step 358 of scanning one section; (5) the step 360 of adjusting the focus again; (6) the step 362 of counting the adjustment; (7) the decision step 364 of determining if it is eight counts, and if not, returning to step 358 and repeating, and if it is, ending the scan; and (8) substep 366 of ending the dynamic focusing operation. With this arrangement, the microscope is refocused eight times in a scan operation.

In FIG. 14, there is shown a program 370 for controlling the scan comprising: (1) the step 372 of beginning the scan; (2) the step 374 in which the customer uses the host computer or scanner keyboard to start scanning; (3) the step 375 in which the scanner software initializes DMA (direct memory access) pointers and initializes a final position in the motor control integrated circuit; (4) the step 376 in which the scanning software tells the motor control integrated circuit to begin moving the microscope; (5) the step 378 in which a traverse of the microscope each 0.00048 inches causes the analog-to-digital converter to take one measurement and store that reading in memory; (6) the step 380 in which the scanner microprocessor is interrupted to say that a run is completed when the motor control integrated circuit is done moving a single one-way trip, either left or right; (7) the step 382 of processing data and sending it to the host computer while the motor is moving and taking data, (8) the decision step 384 to determine if scanning is to be continued, in which case the program returns to step 375 and if not, scanning is terminated at step 386; and (9) the step 386 of terminating the scan. As shown in this diagram, the computer control moves the scanner from place to place taking measurements along a path to perform a scanning operation.

Figure 15:
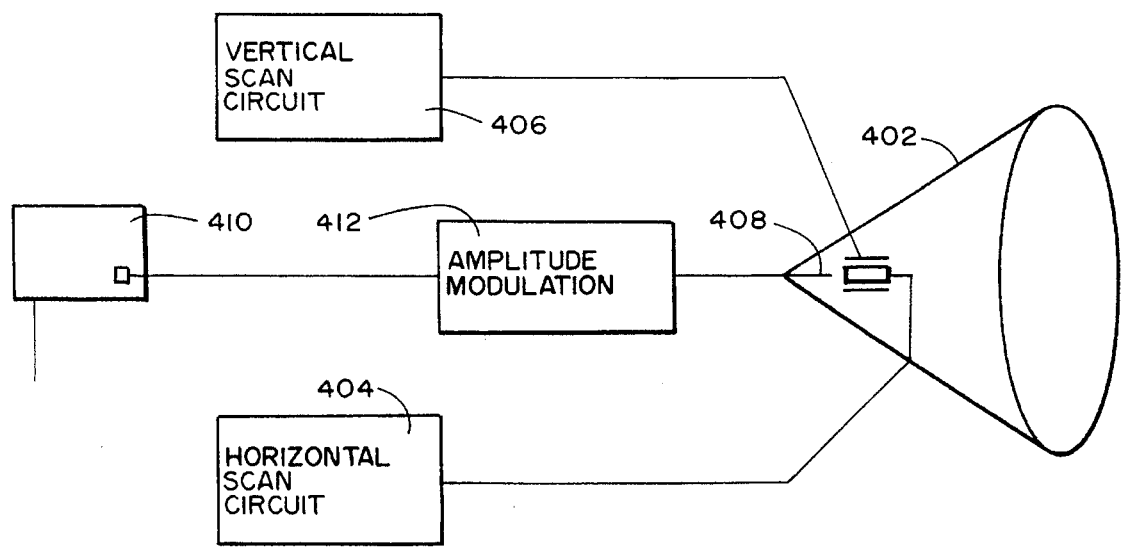
FIG. 15 is a schematic diagram of a display arrangement useful in the embodiment of FIGS. 1–14.
Figure 16:
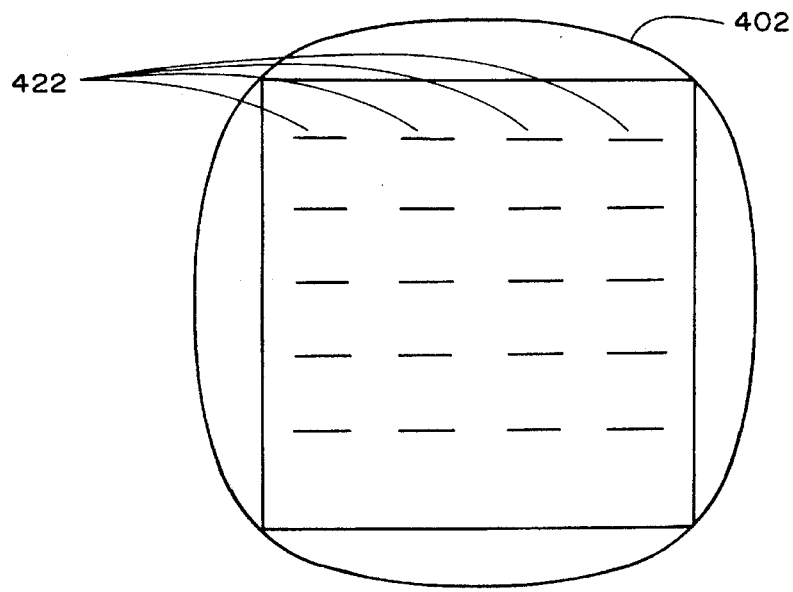
FIG. 16 is a front view of a display screen resulting from its use of the display arrangement of FIG. 15.

In FIG. 15, there is shown a block diagram of the display 400 having a cathode ray tube 402, a horizontal scan circuit 404, a vertical scan circuit 406, an electron gun 408, a driver 410 and an intensity control 412. As shown in this view, the horizontal scan control 404 periodically scans horizontally by applying a voltage to the deflection plates to move an electron beam from the gun 408 horizontally across the screen of the tube 402. At a less rapid rate, the vertical control 406 changes the vertical voltage to deflect the electron beam and form a raster. During the formation of the raster, data is applied to the driver 410 from the computer (FIG. 7) to modulate the voltage in the modulation control 412 to change the intensity corresponding to data. As shown in FIG. 16, the face of the cathode ray tube 402 scans across with its data to form a plurality of bands 422 in which the existence of markers is shown by a different intensity of light on the screen so that DNA channels in the gel are shown as dark and light bands in a manner similar to that shown by gel electrophoresis. With this arrangement, the scanning rate may be set to discriminate against noise, particularly discriminating against the natural fluorescense of the glass in the gel sandwich 150 (FIGS. 3 and 4). The screen display permits easy adjustment during measurements or data retrieval.

From the above summary, it can be understood that the sequencing techniques of this invention have several advantages, such as: (1) they take advantage of resolution over time, as opposed to space; (2) they are continuous; (3) they are automatic; (4) they are capable of sequencing or identifying markers in relatively long strands including strands of more than 100 bases; and (5) they are relatively economical and easy to use.

While in the preferred embodiment, a single emission frequency is used in the infrared region in each channel and for all of A, T, G and C terminated strands with the channel location identifying the terminating base type, multiple fluorescent markers can be used with the wavelength being used to identify the base type. In such an embodiment, an optical means detects a plurality of wavelengths and the computer correlates intensity data, corresponding lanes and corresponding wavelengths.

Although a preferred embodiment of the invention has been described with some particularity, many modifications and variations are possible in the preferred embodiment within the light of the above description. Accordingly, within the scope of the appended claims, the invention may be practiced other than as specifically described.

What is claimed is:

1. Apparatus for sequencing DNA comprising:

a gel electrophoresis slab having an upper portion and a lower portion;

means for applying fluorescently marked DNA samples at a plurality of locations for electrophoresing in a plurality of channels through the gel electrophoresis slab;

means for establishing electrical potential across said gel electrophoresis slab wherein DNA samples are resolved in accordance with the size of DNA fragments in said gel electrophoresis slab into fluorescently marked DNA bands;

means for scanning the separated fluorescently marked DNA bands photoelectrically with a laser and a sensor, wherein the laser scans with a scanning light at a scanning light frequency within an absorbent spectrum of said fluorescently marked DNA samples;

means for sensing light at an emission frequency of the marked DNA;

said means for scanning including means for focusing a microscope on the gel portion of the electrophoresis slab, wherein the bands are scanned while still in the gel but after being resolved;

the means for establishing an electrical potential across said gel electrophoresis slab including an upper buffer assembly connected to an upper end of the slab and a lower buffer assembly connected to a lower portion of the gel electrophoresis slab; and means for positioning the gel electrophoresis slab at any one of a plurality of different elevations, wherein different lengths of gel electrophoresis slabs may be accommodated.

2. Apparatus in accordance with claim 1 in which the means for positioning includes:

a support plate within the apparatus for sequencing DNA;

a plurality of side brackets mounted to one of the support plate and gel electrophoresis slab;

a corresponding plurality of pins mounted to the other of the support plate and gel electrophoresis slab, wherein the gel electrophoresis slab may be mounted by the brackets and pins and different elevations.

3. Apparatus according to claim 2 further including:

means for electrically connecting at least one of the upper and lower buffer compartments to a source of electricity;

said means for connecting being adapted to connect said source of electricity to a buffer compartment that is at any of a plurality of elevations.

4. Apparatus in accordance with claim 1 wherein light from said laser is in the band incorporating at least the near infrared and infrared regions and said sensor responds to light in the band including at least said near infrared and infrared regions.

* * * * *